United States Patent
Gee

(10) Patent No.: US 12,054,443 B2
(45) Date of Patent: Aug. 6, 2024

(54) METHODS FOR MAKING LINEAR INTERNAL OLEFINS FROM MIXTURES OF LINEAR AND BRANCHED OLEFINS

(71) Applicant: Chevron Phillips Chemical Company LP, The Woodlands, TX (US)

(72) Inventor: Jeffery C Gee, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 2 days.

(21) Appl. No.: 17/885,625

(22) Filed: Aug. 11, 2022

(65) Prior Publication Data
US 2024/0051900 A1    Feb. 15, 2024

(51) Int. Cl.
*C07C 1/213* (2006.01)
*B01J 31/10* (2006.01)
(Continued)

(52) U.S. Cl.
CPC .............. *C07C 1/213* (2013.01); *B01J 31/10* (2013.01); *C07C 5/03* (2013.01); *C07C 5/2568* (2013.01);
(Continued)

(58) Field of Classification Search
None
See application file for complete search history.

(56) References Cited

U.S. PATENT DOCUMENTS 2,304,872 A * 12/1942 Bachman ............... C07C 1/213
562/606
4,569,725 A * 2/1986 Lindner .................... C07C 7/17
203/29
(Continued)

FOREIGN PATENT DOCUMENTS

| EP | 1144349 B2 | 10/2011 |
| JP | 2014129271 A | * 7/2014 |
| WO | 2020009750 A1 | 1/2020 |

OTHER PUBLICATIONS

Translation JP 2014129271. Retrieved Mar. 6, 2024. (Year: 2024).*
(Continued)

*Primary Examiner* — In Suk C Bullock
*Assistant Examiner* — Alyssa L Cepluch
(74) *Attorney, Agent, or Firm* — Merchant & Gould P.C.

(57) ABSTRACT

Processes for producing a linear internal olefin product include the steps of contacting an olefin feed containing $C_{10}$-$C_{20}$ vinylidenes and a $C_{10}$-$C_{20}$ normal alpha olefin and/or $C_{10}$-$C_{20}$ linear internal olefins, a first acid catalyst, and a $C_1$ to $C_{18}$ carboxylic acid to form a first reaction product containing linear internal olefins, trisubstituted olefins, and secondary esters, then removing all or a portion of the secondary esters from the first reaction product, followed by contacting the secondary esters and a second acid catalyst to form a second reaction product comprising linear internal olefins, and then removing all or a portion of the linear internal olefins from the second reaction product to form the linear internal olefin product. Linear alkanes subsequently can be produced by hydrogenating the linear internal olefin product to form a linear alkane product.

27 Claims, 2 Drawing Sheets

(51) Int. Cl.
*C07C 5/03* (2006.01)
*C07C 5/25* (2006.01)

(52) U.S. Cl.
CPC .... *B01J 2231/005* (2013.01); *B01J 2531/002* (2013.01); *C07C 2527/03* (2013.01)

(56) References Cited

U.S. PATENT DOCUMENTS

| | | |
|---|---|---|
| 5,284,988 A | 2/1994 | Schaerl, Jr. |
| 5,322,633 A | 6/1994 | Senaratne |
| 6,100,223 A | 8/2000 | Gee |
| 6,191,076 B1 | 2/2001 | Gee |
| 6,407,302 B1 | 6/2002 | Twu |
| 7,332,637 B2 | 2/2008 | Gee |
| 9,365,788 B2 | 6/2016 | Emett |
| 9,399,746 B2 | 7/2016 | Emett |
| 9,796,645 B2 | 10/2017 | Emett |
| 2004/0249229 A1* | 12/2004 | Gee ................ C07C 5/2568 585/671 |
| 2007/0049784 A1 | 3/2007 | Gee |
| 2007/0281875 A1* | 12/2007 | Scheibel .............. C10G 3/50 585/324 |
| 2020/0369579 A1* | 11/2020 | Son ...................... C07C 7/04 |

OTHER PUBLICATIONS

International Search Report and Written Opinion issued in corresponding PCT No. PCT/US2023/071971 mailed on Nov. 30, 2023. 11 pp.

\* cited by examiner

METHODS FOR MAKING LINEAR INTERNAL OLEFINS FROM MIXTURES OF LINEAR AND BRANCHED OLEFINS

FIELD OF THE INVENTION

The present disclosure concerns processes for producing linear internal olefins and linear alkanes. More particularly, the present disclosure relates to producing such linear internal olefins and linear alkanes from a mixture of linear and branched olefins using a multistep process.

BACKGROUND OF THE INVENTION

There are many end-use applications in which high purity linear internal olefins or high purity linear alkanes are desired. A non-limiting example is a thermal switch, which requires a sharp melting or freezing point. Many internal olefin and normal alpha olefin feedstocks (e.g., with carbon numbers of ten or more) contain vinylidenes, which are very difficult to separate from the linear olefins by distillation. Subsequent hydrogenation therefore produces methyl branched alkanes that can decrease the value of the desired linear alkane product. Thus, there is a need to provide a different route for producing linear olefins and linear alkanes in which branching is significantly reduced or eliminated. Accordingly, it is to this end that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for producing linear internal olefins are disclosed herein. These processes can comprise (a) contacting an olefin feed comprising $C_{10}$ to $C_{20}$ vinylidenes and a $C_{10}$ to $C_{20}$ normal alpha olefin and/or $C_{10}$ to $C_{20}$ linear internal olefins, a first acid catalyst, and a $C_1$ to $C_{18}$ carboxylic acid to form a first reaction product comprising linear internal olefins, trisubstituted olefins, and secondary esters, (b) removing all or a portion of the secondary esters from the first reaction product, (c) contacting the secondary esters and a second acid catalyst to form a second reaction product comprising linear internal olefins, and (d) removing all or a portion of the linear internal olefins from the second reaction product to form a linear internal olefin product. Although not limited thereto, the first acid catalyst and the second acid catalyst can be solid acid catalysts.

Processes for producing linear alkanes also are disclosed herein. These processes can be performed similarly to the processes for producing linear internal olefins, but further comprising a step (e) of hydrogenating the linear internal olefin product to form a linear alkane product.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description and examples.

DEFINITIONS

Figure 1:
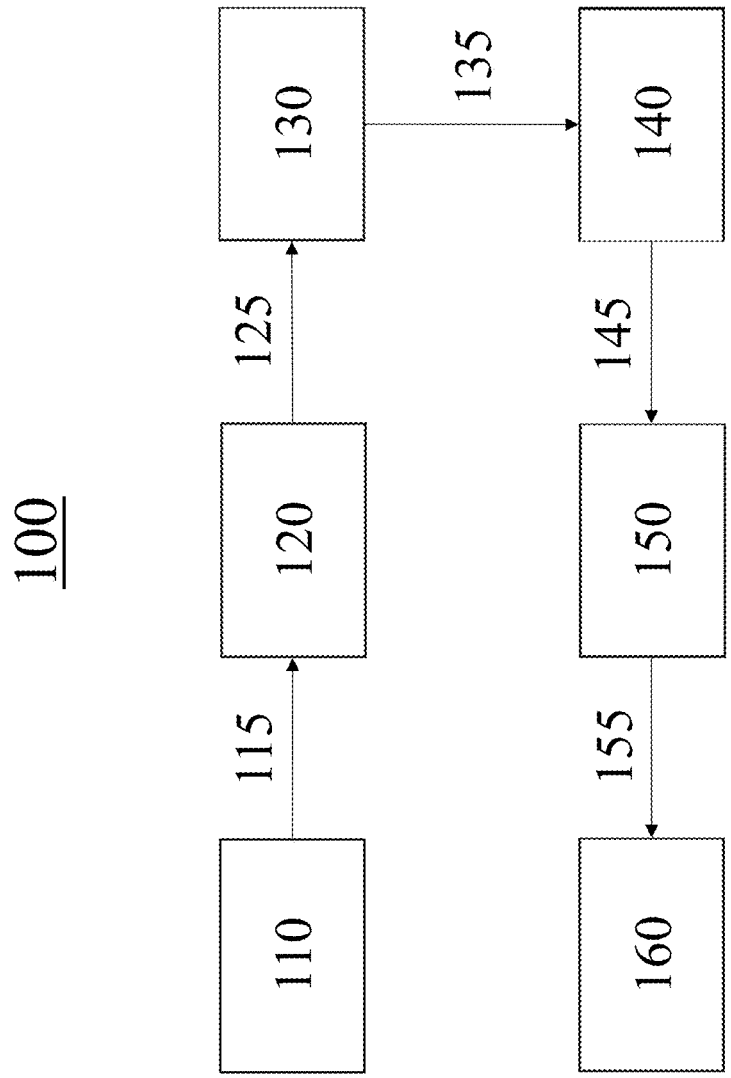
FIG. 1 presents a schematic flow diagram of a process for producing linear internal olefins and linear alkanes consistent with aspects of this invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and/or feature disclosed herein, all combinations that do not detrimentally affect the systems, compositions, processes, and/or methods described herein are contemplated with or without explicit description of the particular combination. Additionally, unless explicitly recited otherwise, any aspect and/or feature disclosed herein can be combined to describe conceived processes and systems consistent with the present disclosure.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise. The terms "a," "an," and "the" are intended to include plural alternatives, e.g., at least one, unless otherwise specified. For instance, the disclosure of "a normal alpha olefin" or "an acid catalyst" is meant to encompass one, or mixtures or combinations of more than one, normal alpha olefin or acid catalyst, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique. Herein, "contacting" or "combining" two or more components can result in a reaction product.

The term "hydrocarbon" refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon).

The term "alkane" refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane).

The term "olefin" refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to any olefin that has 1) a carbon-carbon double bond between the first and second carbon atom of the longest contiguous chain of carbon atoms, and 2) at least one hydrogen atom bound to the second carbon of the chain. The term "alpha olefin" includes linear and branched alpha olefins and alpha olefins which can have more than one non-aromatic carbon-carbon double bond, unless expressly stated otherwise. In the case of branched olefins, a branch can be at the 2-position of a 1-alkene (a vinylidene) with respect to the olefin double bond. Thus, the term "vinylidene" refers to a 1-alkene having an alkyl branch at the 2-position with respect to the olefin double bond. The term "normal alpha olefin" refers to a linear aliphatic hydrocarbon mono-olefin having 1) a carbon-carbon double bond between the first and second carbon atoms, and 2) at least one hydrogen atom bound to the second carbon of the chain. The term "linear internal olefin" refers to a linear aliphatic hydrocarbon mono-olefin having a double bond that is not between the first and second carbon atoms.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, there can be a range of weight ratios of the olefin feed to the first acid catalyst in aspects of this invention. By a disclosure that weight ratio is in a range from 1:1 to 100:1, the intent is to recite that the weight ratio can be any amount in the range and, for example, can include any range or combination of ranges from 1:1 to 100:1, such as from 1:1 to 10:1, from 1.5:1 to 40:1, or from 1.5:1 to 15:1, and so forth. Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods and materials similar or equivalent to those described herein can be used in the practice or testing of the processes and reaction systems, the typical methods and materials are herein described.

All publications and patents mentioned herein are incorporated herein by reference in their entirety for the purpose of describing and disclosing, for example, the constructs and methodologies that are described in the publications and patents, which might be used in connection with the present disclosure.

DETAILED DESCRIPTION OF THE INVENTION

Disclosed herein are processes for producing linear internal olefins and linear alkanes from a mixture of linear and branched olefins, such as vinylidenes, using a multistep process.

Methods for Making Linear Internal Olefins

The processes for producing linear internal olefins disclosed herein can comprise (or consist essentially of, or consist of) (a) contacting (in any order) an olefin feed comprising $C_{10}$ to $C_{20}$ vinylidenes and a $C_{10}$ to $C_{20}$ normal alpha olefin and/or $C_{10}$ to $C_{20}$ linear internal olefins, a first acid catalyst, and a $C_1$ to $C_{18}$ carboxylic acid to form a first reaction product comprising linear internal olefins, trisubstituted olefins, and secondary esters, (b) removing all or a portion of the secondary esters from the first reaction product, (c) contacting the secondary esters and a second acid catalyst to form a second reaction product comprising linear internal olefins, and (d) removing all or a portion of the linear internal olefins from the second reaction product to form a linear internal olefin product. Generally, the features of the processes (e.g., the olefin feed, the reaction conditions under which step (a) is performed, the first reaction product, the secondary esters, the reaction conditions under which step (c) is performed, the second reaction product, and the linear internal olefin product, among others) are independently described herein, and these features can be combined in any combination to further describe the disclosed processes. Moreover, additional process steps can be performed before, during, and/or after any of the steps of any of the processes disclosed herein, unless stated otherwise. Further, linear internal olefin products produced by any of the disclosed processes also are encompassed herein.

The olefin feed in step (a) comprises $C_{10}$ to $C_{20}$ vinylidenes and a $C_{10}$ to $C_{20}$ normal alpha olefin and/or $C_{10}$ to $C_{20}$ linear internal olefins, thus, the olefin feed can comprise $C_{10}$ to $C_{20}$ vinylidenes and a $C_{10}$ to $C_{20}$ normal alpha olefin, or $C_{10}$ to $C_{20}$ vinylidenes and $C_{10}$ to $C_{20}$ linear internal olefins, or $C_{10}$ to $C_{20}$ vinylidenes and a $C_{10}$ to $C_{20}$ normal alpha olefin and $C_{10}$ to $C_{20}$ linear internal olefins. In one aspect, the olefin feed can comprise $C_{12}$ to $C_{20}$ vinylidenes (and a $C_{12}$ to $C_{20}$ normal alpha olefin and/or $C_{12}$ to $C_{20}$ linear internal olefins), while in another aspect, the olefin feed can comprise $C_{14}$ to $C_{18}$ vinylidenes (and a $C_{14}$ to $C_{18}$ normal alpha olefin and/or $C_{14}$ to $C_{18}$ linear internal olefins), and in yet another aspect, the olefin feed can comprise $C_{16}$ to $C_{18}$ vinylidenes (and a $C_{16}$ to $C_{18}$ normal alpha olefin and/or $C_{10}$ to $C_{18}$ linear internal olefins). For instance, the $C_{10}$ to $C_{20}$ normal alpha olefin in the olefin feed can comprise (or consist essentially of, or consist of) 1-decene, 1-dodecene, 1-tetradecene, 1-hexadecene, 1-octadecene, or any combination thereof; alternatively, 1-decene; alternatively, 1-dodecene; alternatively, 1-tetradecene; alternatively, 1-hexadecene; or alternatively, 1-octadecene. Thus, mixtures of various normal alpha olefins having different numbers of carbon atoms can be present in the olefin feed, or normal alpha olefins having predominantly a single number of carbon atoms can be present in the olefin feed. While a mixture of different carbon number olefins can be present in the olefin feed, the processes disclosed herein are particularly well suited for use with olefin feeds having a single carbon number.

Any suitable amount of the olefin feed can be the normal alpha olefin, the linear internal olefins, or a mixture of both. Generally, the olefin feed contains at least 50 wt. % of the $C_{10}$ to $C_{20}$ normal alpha olefin and/or $C_{10}$ to $C_{20}$ linear internal olefins, and more often, contains at least 60 wt. %, at least 70 wt. %, at least 80 wt. %, at least 90 wt. %, at least 92 wt. %, or at least 95 wt. % of the $C_{10}$ to $C_{20}$ normal alpha olefin and/or $C_{10}$ to $C_{20}$ linear internal olefins, and in some aspects, less than or equal to 99 wt. %, less than or equal to 98 wt. %, less than or equal to 97 wt. %, or less than or equal to 96 wt. % of the $C_{10}$ to $C_{20}$ normal alpha olefin and/or $C_{10}$ to $C_{20}$ linear internal olefins, and in some aspects, a range from any minimum amount disclosed herein to any maximum amount disclosed herein of the $C_{10}$ to $C_{20}$ normal alpha olefin and/or $C_{10}$ to $C_{20}$ linear internal olefins. Likewise, the olefin feed can contain these same minimum amounts, maximum amounts, and ranges for any combination of single carbon numbered normal alpha olefins and linear internal olefins described herein; or alternatively, of any single carbon numbered normal alpha olefin or linear internal olefins described herein. For instance, in a non-limiting example, the olefin feed can comprise at least 50 wt. %, at least 60 wt. %, at least 70 wt. %, at least 80 wt. %, at least 90 wt. %, at least 92 wt. %, or at least 95 wt. %, and less than or equal to 99 wt. %, less than or equal to 98 wt. %, less than or equal to 97 wt. %, or less than or equal to 96 wt. % (e.g., a range from any minimum amount disclosed herein to any maximum amount disclosed herein) of 1-decene; alternatively, 1-decene and $C_{10}$ linear internal olefins; alternatively, 1-dodecene; alternatively, 1-dodecene and $C_{12}$ linear internal olefins; alternatively, 1-tetradecene; alternatively, 1-tetradecene and $C_{14}$ linear internal olefins; alternatively, 1-hexadecene; alternatively, 1-hexadecene and $C_{16}$ linear internal olefins; alternatively, 1-octadecene; or alternatively, 1-octadecene and $C_{18}$ linear internal olefins.

Consistent with these and other aspects of this invention, the relative amount of normal alpha olefin to linear internal olefins in the olefin feed is not particularly limited, but generally ranges from 100:1 to 1:100 on a weight basis. In one aspect, therefore, the olefin feed can be characterized by a weight ratio of $C_{10}$ to $C_{20}$ normal alpha olefin to $C_{10}$ to $C_{20}$ linear internal olefins in a range from 50:1 to 1:50, while in another aspect, the weight ratio can be from 10:1 to 1:10, and from 5:1 to 1:5 in yet another aspect, and from 2:1 to 1:2 in still another aspect.

In addition to normal alpha olefins and linear internal olefins, the olefin feed also contains branched olefins, such as vinylidenes, but typically the branched olefin content is a smaller fraction of the olefin feed. Often, the $C_{10}$ to $C_{20}$ vinylidenes constitute less than or equal to 50 wt. %, less than or equal to 35 wt. %, less than or equal to 20 wt. %, or less than or equal to 10 wt. %, of the olefin feed, but at least 1 wt. %, at least 1.5 wt. %, at least 2 wt. %, at least 4 wt. %, or at least 5 wt. %, of the olefin feed. Thus, the olefin feed can contain any amount of $C_{10}$ to $C_{20}$ vinylidenes between these respective minimum and maximum amounts, such as from 1 to 50 wt. %, from 1.5 to 35 wt. %, from 2 to 35 wt. %, from 2 to 10 wt. %, from 4 to 20 wt. %, from 4 to 10 wt. %, or from 5 to 50 wt. %, and the like.

The $C_1$ to $C_{18}$ carboxylic acid used in the process is not particularly limited. The carboxylic acid can be a $C_1$ to $C_{12}$ carboxylic acid or a $C_1$ to $C_8$ carboxylic acid in some aspects, while the carboxylic acid can be a $C_2$ to $C_8$ carboxylic acid or a $C_{12}$ to $C_{18}$ carboxylic acid in other aspects. Representative and non-limiting examples of carboxylic acids that can be used in the processes disclosed herein include formic acid, acetic acid, propionic acid, butyric acid, pentanoic acid, hexanoic acid, heptanoic acid, octanoic acid, nonanoic acid, decanoic acid, and the like, as well as any combination thereof. In an aspect, the carboxylic acid can comprise formic acid; alternatively, acetic acid; alternatively, propionic acid; alternatively, butyric acid; alternatively, pentanoic acid; alternatively, hexanoic acid; alternatively, heptanoic acid; alternatively, octanoic acid; alternatively, nonanoic acid; or alternatively, decanoic acid.

Certain ratios of components during step (a) can prove advantageous with respect to the amount of linear internal olefins, trisubstituted olefins, and secondary esters in the first reaction product. For instance, the molar ratio of the moles of the carboxylic acid to moles of olefin in the olefin feed in step (a) can range from 10:1 to 1:10. Accordingly, suitable non-limiting ranges for the molar ratio of moles of the carboxylic acid to moles of olefin in the olefin feed in step (a) can include the following: from 5:1 to 1:5, from 4:1 to 1:4, from 3:1 to 1:3, from 1.5:1 to 1:1.5, or from 1.2:1 to 1:1.2 (carboxylic acid:olefin), and the like.

Additionally or alternatively, on a weight basis, the amount of the carboxylic acid based on the olefin feed is typically less than or equal to 75 wt. %, less than or equal to 60 wt. %, or less than or equal to 50 wt. %, and in some aspects, at least 1 wt. %, at least 5 wt. %, at least 10 wt. %, at least 20 wt. %, or at least 25 wt. %. Often, the amount of the carboxylic acid based on the weight of the olefin feed can range from any minimum amount disclosed herein to any maximum amount disclosed herein.

Generally, the appropriate procedure for contacting (or reacting) the olefin feed (which contains $C_{10}$ to $C_{20}$ vinylidenes and a $C_{10}$ to $C_{20}$ normal alpha olefin and/or $C_{10}$ to $C_{20}$ linear internal olefins), the first acid catalyst, and the $C_1$ to $C_{18}$ carboxylic acid is not particularly limited. For instance, the olefin feed, the first acid catalyst, and the $C_1$ to $C_{18}$ carboxylic acid can be contacted in any order, method, or process that produces a first reaction product having an acceptable amount of linear internal olefins, trisubstituted olefins, and secondary esters. Nonetheless, in an aspect, a mixture of the olefin feed and the carboxylic acid can be contacted with the first acid catalyst (e.g., solid acid catalyst) in step (a).

It can be beneficial to conduct step (a) in an environment that is substantially free of water/moisture. Thus, all raw materials and the atmosphere in step (a) of the process can be dry and substantially free of water/moisture. Thus, aspects of this invention are directed to the process where step (a) is conducted in the presence of less than or equal to 1 wt. % water/moisture, and more often, in the presence of less than or equal to 0.5 wt. %, less than or equal to 1000 ppm (by weight), less than or equal to 500 ppm, or less than or equal to 200 ppm water/moisture, but often greater than 0 ppm, at least 1 ppm, at least 10 ppm, at least 25 ppm, or at least 50 ppm water/moisture.

In an aspect, step (a) of the process can be conducted at any temperature below the maximum operating temperature (or thermal stability temperature) of the first acid catalyst, when the first acid catalyst is a solid acid catalyst. In another aspect, step (a) of the process can be conducted at any temperature below the melting temperature of the first acid catalyst, when the first acid catalyst is a solid acid catalyst, or step (a) of the process can be conducted at any temperature below the softening point/temperature of the first acid catalyst, when the first acid catalyst is a solid acid catalyst. For instance, and depending upon the particular (solid) acid catalyst, step (a) can be conducted at a minimum temperature of 10° C., 20° C., 50° C., 70° C., or 80° C.; additionally or alternatively, at a maximum temperature 180° C., 150° C., 120° C., 110° C., 105° C., or 100° C. Generally, the temperature for step (a) can be in a range from any minimum temperature disclosed herein to any maximum temperature disclosed herein. Accordingly, suitable non-limiting ranges for temperature of step (a) and for the formation of the first reaction product can include the following: from 10° C. to 180° C., from 70° C. to 180° C., from 20° C. to 150° C., from 50° C. to 150° C., from 80° C. to 150° C., from 10° C. to 120° C., from 50° C. to 120° C., from 20° C. to 110° C., from 50° C. to 110° C., from 70° C. to 110° C., from 80° C. to 105° C., from 20° C. to 100° C., or from 70° C. to 100° C. These temperature ranges also are meant to encompass circumstances where step (a) of the process (or the formation of the first reaction product) is performed at a series of different temperatures, instead of at a single fixed temperature, falling within the respective temperature ranges.

The pressure used for step (a) of the process and/or for the formation of the first reaction product is not particularly limited. For instance, step (a) of the process can be conducted at a pressure in a range from 5 psig to 100 psig; alternatively, at atmospheric pressure; or alternatively, at a sub-atmospheric pressure.

In an aspect, step (a) of the process can be conducted in a stirred tank reactor. The time period for contacting the olefin feed, the carboxylic acid, and the first acid catalyst (or for the formation of the first reaction product) in the stirred tank reactor is not particularly limited, and can be conducted for any suitable period of time. Nonetheless, the minimum average residence time in the stirred tank reactor for step (a) can be 5 min, 10 min, 15 min, 30 min, or 1 hr; additionally or alternatively, the maximum average residence time can be 10 hr, 8 hr, 7 hr, 5 hr, or 3 hr. Generally, the average residence time in the stirred tank reactor for step (a) of the process can be in a range from any minimum time disclosed herein to any maximum time disclosed herein. Accordingly, suitable non-limiting ranges for the average residence time can include the following: from 5 min to 10 hr, from 10 min to 8 hr, from 15 min to 7 hr, from 30 min to 5 hr, from 30 min to 3 hr, from 1 hr to 10 hr, from 1 hr to 7 hr, from 1 hr to 5 hr, or from 1 hr to 3 hr.

The weight ratio of the olefin feed to the first acid catalyst (olefin:catalyst) in the stirred tank reactor is not particularly limited. In an aspect, step (a) of the process can be conducted at a minimum weight ratio of olefin:catalyst of 1:1, 1.5:1, or 5:1; additionally or alternatively, step (a) of the process can be conducted at a maximum weight ratio of olefin:catalyst of 100:1, 40:1, 15:1, or 10:1. Generally, the olefin:catalyst weight ratio can be in a range from any minimum weight ratio disclosed herein to any maximum weight ratio disclosed herein. Accordingly, suitable non-limiting ranges for the olefin:catalyst weight ratio can include from 1:1 to 100:1, from 1:1 to 10:1, from 1.5:1 to 40:1, from 1.5:1 to 15:1, from 5:1 to 100:1, from 5:1 to 40:1, or from 5:1 to 15:1.

In an aspect, step (a) of the process can be conducted in a fixed bed reactor. In such aspects, the olefin feed-solid catalyst contact time (or reaction time) can be expressed in terms of weight hourly space velocity (WHSV)—the ratio of the weight of the olefin feed which comes in contact with a given weight of the first solid acid catalyst per unit time (units of g/g/hr). While not limited thereto, step (a) of the process can be conducted at a minimum WHSV value of 0.05, 0.1, or 0.2; additionally or alternatively, step (a) of the process can be conducted at a maximum WHSV value of 5, 2, or 1. Generally, the WHSV can be in a range from any minimum WHSV disclosed herein to any maximum WHSV disclosed herein. Accordingly, suitable non-limiting ranges for the WHSV can include the following: from 0.05 to 5, from 0.2 to 5, from 0.1 to 5, from 0.1 to 2, from 0.1 to 1, from 0.2 to 5, from 0.2 to 2, or from 0.2 to 1.

In some aspects, step (a) of the process can include contacting the olefin feed, the first acid catalyst, the carboxylic acid, and optionally, additional unrecited materials (e.g., a non-olefin solvent or diluent, a stabilizer, amongst other materials). Thus, for example, step (a) of the process can be performed (or the first reaction product can be formed) in the presence of a non-olefin solvent. The amount of any non-olefin solvent used in addition to olefin feed in step (a) of the process is not limited to any particular range. Such solvent, or combination of solvents, can be used, for example, as a flow modifier to alter the flow properties or viscosity of the olefin feed and/or the flow properties of the first reaction product. When a non-olefin solvent is used, step (a) of the process can be conducted in the presence of less than or equal to 25 wt. %, less than or equal to 10 wt. %, or less than or equal to 5 wt. %, and greater than 0 wt. %, at least 0.5 wt. %, at least 1 wt. %, or at least 2 wt. %, of the non-olefin solvent, based on the olefin feed. In some aspects, no additional solvent is used, so a further removal step for the solvent is not needed.

When a non-olefin solvent is used, illustrative non-olefin organic solvents which can be utilized in step (a) of the process disclosed herein can include alkanes (e.g., pentane, hexane, heptane, octane, cyclohexane), aromatics (e.g., benzene, toluene, xylene, ethylbenzene), halogenated hydrocarbons (e.g., carbon tetrachloride, methylene chloride, chlorobenzene), and the like. Combinations of two or more non-olefin solvents also can be utilized.

The contacting of the olefin feed (containing $C_{10}$ to $C_{20}$ vinylidenes and a $C_{10}$ to $C_{20}$ normal alpha olefin and/or $C_{10}$ to $C_{20}$ linear internal olefins), the first acid catalyst (e.g., a solid acid catalyst), and the $C_1$ to $C_{18}$ carboxylic acid forms the first reaction product, which contains linear internal olefins, trisubstituted olefins, and secondary esters. If the first acid catalyst is a solid acid catalyst, the first reaction product can be readily separated from the first solid acid catalyst (or the first solid acid catalyst can be readily separated from the first reaction product) using any suitable technique, such as filtration. In the first reaction product, often the secondary esters are present as mixture of isomers.

The first reaction product generally contains less than or equal to 10 wt. % of $C_{10}$ to $C_{20}$ normal alpha olefin, and more often, contains less than or equal to 8 wt. %, less than or equal to 5 wt. %, less than or equal to 3 wt. %, or less than or equal to 1 wt. %, of $C_{10}$ to $C_{20}$ normal alpha olefin, and often can contain greater than 0 wt. %, at least 0.1 wt. %, at least 0.5 wt. %, or at least 0.75 wt. % of $C_{10}$ to $C_{20}$ normal alpha olefin. The first reaction product also can contain an amount of $C_{10}$ to $C_{20}$ normal alpha olefin in a range from any minimum amount disclosed herein to any maximum amount disclosed herein.

Likewise, the first reaction product typically contains less than or equal to 10 wt. % dimer (formed from the original $C_{10}$ to $C_{20}$ normal alpha olefin in the olefin feed), and more often, less than or equal to 8 wt. %, less than or equal to 5 wt. %, less than or equal to 3 wt. %, or less than or equal to 1 wt. %, of dimer, and often can contain greater than 0 wt. %, at least 0.1 wt. %, at least 0.5 wt. %, or at least 0.75 wt. % of dimer. The first reaction product also can contain an amount of dimer in a range from any minimum amount disclosed herein to any maximum amount disclosed herein.

Since there is some amount of branched olefins (e.g., vinylidenes) in the olefin feed, in addition to the normal alpha olefin and linear internal olefins, the first reaction product also can contain branched olefins (e.g., trisubstituted olefins). Often, the trisubstituted olefins constitute less than or equal to 15 wt. %, less than or equal to 12 wt. %, less than or equal to 10 wt. %, or less than or equal to 8 wt. %, of the first reaction product, but at least 1 wt. %, at least 1.5 wt. %, at least 2 wt. %, at least 4 wt. %, or at least 5 wt. %, of the first reaction product. Thus, the first reaction product can contain any amount of trisubstituted olefins between these respective minimum and maximum amounts, such as from 1 to 15 wt. %, from 1.5 to 12 wt. %, from 2 to 12 wt. %, from 4 to 12 wt. %, from 4 to 8 wt. %, from 5 to 15 wt. %, or from 5 to 10 wt. %, and the like.

However, the amount of additional branched olefins over the amount originating in the olefin feed is typically very small. For instance, the first reaction product often contains less than or equal to 5 wt. %, less than or equal to 4 wt. %, less than or equal to 2 wt. %, less than or equal to 1 wt. %, or less than or equal to 0.5 wt. %, more branched olefins than an amount of branched olefins in the olefin feed. In some aspects, the amount of branched olefins in the first reaction product is the same as the amount of branched olefins in the olefin feed (i.e., additional branched olefins are not being produced in step (a)).

Depending upon the reaction conditions, the first reaction product can comprise a nearly equilibrium distribution of linear double bond isomers, although this is not a requirement.

The first reaction product can contain any suitable amount of secondary esters, but generally, the amount of secondary esters in the first reaction product ranges from 10 to 50 mol %, based on the moles of the $C_{10}$ to $C_{20}$ normal alpha olefin and/or $C_{10}$ to $C_{20}$ linear internal olefins in the olefin feed. For example, the first reaction product can comprise from 20 to 50 mol % secondary esters, from 25 to 50 mol % secondary esters, or from 30 to 50 mol % secondary esters, based on the moles of the $C_{10}$ to $C_{20}$ normal alpha olefin and/or $C_{10}$ to $C_{20}$ linear internal olefins in the olefin feed.

Referring now to step (b) of the process, all or a portion of the secondary esters is removed from the first reaction product. This can be accomplished using any suitable technique, which can include but is not limited to, flashing, wiped film evaporation, distillation, short path distillation, or any combination thereof.

If desired, the linear internal olefins, the trisubstituted olefins, the residual carboxylic acid, or any combination of these materials, are recovered from the first reaction product. Optionally, any of these materials, such as the carboxylic acid, can be recycled in the process.

In step (c), the secondary esters (from the first reaction product) and a second acid catalyst (e.g., a solid acid catalyst) are contacted to form a second reaction product comprising linear internal olefins. Step (c) can be performed in a similar manner to that of step (a), and thus the features disclosed herein for step (a) are also applicable to step (c). Accordingly, step (c) can be conducted in the substantial absence of water/moisture like step (a), and at temperature and pressure conditions that are the same as those provided herein for step (a). The second (solid) acid catalyst can be the same as or different from the first (solid) acid catalyst.

Similar to step (a), an optional non-olefin solvent—any suitable non-olefin solvent disclosed herein—can be used in step (c) at an amount of the non-olefin solvent, based on the secondary esters, of less than or equal to 25 wt. %, less than or equal to 10 wt. %, or less than or equal to 5 wt. %, and greater than 0 wt. %, at least 0.5 wt. %, at least 1 wt. %, or at least 2 wt. %. In some aspects, no additional solvent is used in step (c), so a further removal step for the solvent is not needed.

Like step (a) of the process, step (c) can be conducted in a stirred tank reactor. The time period for contacting the secondary esters and the second acid catalyst (or for the formation of the second reaction product) in the stirred tank reactor is not particularly limited, and can be conducted for any suitable period of time. The average residence time in the stirred tank reactor for step (c) of the process can be in a range from any minimum time disclosed herein to any maximum time disclosed herein for step (a). The ranges for the weight ratio of the secondary esters to the second acid catalyst (esters:catalyst) also are similar to those in step (a), such as weight ratios of esters:catalyst of from 1:1 to 100:1, from 1:1 to 10:1, from 1.5:1 to 40:1, from 1.5:1 to 15:1, from 5:1 to 100:1, from 5:1 to 40:1, or from 5:1 to 15:1.

In another aspect, step (c) of the process—similar to step (a)—can be conducted in a fixed bed reactor, where the ester feed-solid catalyst contact time (or reaction time) can be expressed in terms of weight hourly space velocity (WHSV)—the ratio of the weight of the secondary esters which comes in contact with a given weight of the second solid acid catalyst per unit time (units of g/g/hr). Non-limiting ranges for the WHSV in step (c) can include the from 0.05 to 5, from 0.2 to 5, from 0.1 to 5, from 0.1 to 2, from 0.1 to 1, from 0.2 to 5, from 0.2 to 2, or from 0.2 to 1.

The contacting of the secondary esters and the second (solid) acid catalyst in step (c) forms a second reaction product comprising linear internal olefins. The second reaction product can further contain the $C_1$ to $C_{18}$ carboxylic acid used in step (a). If the second acid catalyst is a solid acid catalyst, the second reaction product can be readily separated from the second solid acid catalyst (or the second solid acid catalyst can be readily separated from the second reaction product) using any suitable technique, such as filtration.

Based on hydrocarbons, the second reaction product can contain at least 90 wt. % of linear olefins, and more often, at least 95 wt. %, at least 97 wt. %, at least 98 wt. %, or at least 99 wt. %, of linear olefins, based on hydrocarbons in the second reaction product, and in some aspects, the second reaction product can contain less than 100 wt. %, less than or equal to 99.99 wt. %, less than or equal to 99.9 wt. %, or less than or equal to 99.5 wt. % of linear olefins. The second reaction product also can contain an amount of linear internal olefins in a range from any minimum amount disclosed herein to any maximum amount disclosed herein. Unexpectedly, and beneficially, this linear olefin product is more linear than that of starting olefin feed.

The second reaction product generally contains less than or equal to 4 wt. % of branched olefins, and more often, contains less than or equal to 3 wt. %, less than or equal to 2 wt. %, less than or equal to 1 wt. %, or less than or equal to 0.5 wt. %, of branched olefins, based on hydrocarbons in the second reaction product, and often can contain greater than 0 wt. %, at least 0.1 wt. %, at least 0.25 wt. %, or at least 0.4 wt. % of branched olefins. The second reaction product also can contain an amount of branched olefins in a range from any minimum amount disclosed herein to any maximum amount disclosed herein.

Referring now to step (d) of the process, all or a portion of the linear internal olefins is removed from the second reaction product to form a linear internal olefin product. This can be accomplished using any suitable technique, which can include but is not limited to, flashing, wiped film evaporation, distillation, short path distillation, or any combination thereof.

If desired, the linear internal olefins, the residual ester, the second carboxylic acid, or a combination of these materials is recovered from the second reaction product. Optionally, any of these materials can be recycled at an appropriate stage of the process.

The linear internal olefin product in step (d) is highly linear. The linear internal olefin product can contain, for instance, at least 90 wt. % linear internal olefin, and more often, contains at least 95 wt. %, at least 97 wt. %, at least 98 wt. %, or at least 99 wt. %, of linear internal olefin, and in some aspects, the linear internal olefin product can contain less than 100 wt. %, less than or equal to 99.99 wt. %, less than or equal to 99.9 wt. %, or less than or equal to 99.5 wt. % of linear internal olefin. The linear internal olefin product also can contain an amount of linear internal olefin in a range from any minimum amount disclosed herein to any maximum amount disclosed herein.

Therefore, the linear internal olefin product contains only a minor amount of branched olefins, such as less than or equal to 4 wt. %, and more often, less than or equal to 3 wt. %, less than or equal to 2 wt. %, less than or equal to 1 wt. %, or less than or equal to 0.5 wt. %, of branched olefins. In some aspects, the linear internal olefin product can contain greater than 0 wt. %, at least 0.1 wt. %, at least 0.25 wt. %, or at least 0.4 wt. %, of branched olefins, and therefore, the linear internal olefin product can contain an amount of branched olefins in a range from any minimum amount disclosed herein to any maximum amount disclosed herein.

Methods for Making Linear Alkanes

Optionally, the process disclosed herein can further comprise a step of (e) hydrogenating the linear internal olefin product to form a linear alkane product. Thus, this process for producing linear alkanes can comprise (a) contacting an olefin feed comprising $C_{10}$ to $C_{20}$ vinylidenes and a $C_{10}$ to $C_{20}$ normal alpha olefin and/or $C_{10}$ to $C_{20}$ linear internal olefins, a first acid catalyst, and a $C_1$ to $C_{18}$ carboxylic acid to form a first reaction product comprising linear internal olefins, trisubstituted olefins, and secondary esters, (b) removing all or a portion of the secondary esters from the first reaction product, (c) contacting the secondary esters and a second acid catalyst to form a second reaction product comprising linear internal olefins, (d) removing all or a portion of the linear internal olefins from the second reaction product to form a linear internal olefin product, and (e) hydrogenating the linear internal olefin product to form a linear alkane product.

For step (e), suitable hydrogenation procedures and associated metal catalysts (e.g., platinum, rhenium, palladium, nickel, etc.) are well known to those of skill in the art. In a representative procedure, the linear internal olefin product can be hydrogenated by contacting the olefin product with 5 wt. % (based on the olefin product) of a nickel hydrogenation catalyst (Crossfield HTC 500) in an autoclave reactor, flushing with nitrogen to replace any residual air, followed by flushing with low pressure hydrogen several times. The reactor then can be pressurized with hydrogen to a suitable pressure (e.g., 500 psig), followed by slowly increasing the temperature from ambient to 180° C. The hydrogenation temperature can be increased to 200° C. (or more) and hydrogen pressure increased to 2000 psig and maintained at that pressure for a time sufficient to complete the hydrogenation (e.g., 2 to 6 hr). Subsequently, the reactor contents can be cooled to ambient temperature and residual catalyst removed to result in the linear alkane product.

Similar to the linear internal olefin product in step (d), the linear alkane product in step (e) also is highly linear. The linear alkane product can contain, for instance, at least 90 wt. % of linear alkane, and more often, contains at least 95 wt. %, at least 97 wt. %, at least 98 wt. %, or at least 99 wt. %, of linear alkane. In some aspects, the linear alkane product can contain less than 100 wt. %, less than or equal to 99.99 wt. %, less than or equal to 99.9 wt. %, or less than or equal to 99.5 wt. % of linear alkane. The linear alkane product also can contain an amount of linear alkane in a range from any minimum amount disclosed herein to any maximum amount disclosed herein.

Therefore, the linear alkane product contains only a minor amount of branched alkanes, such as less than or equal to 4 wt. %, and more often, less than or equal to 3 wt. %, less than or equal to 2 wt. %, less than or equal to 1 wt. %, or less than or equal to 0.5 wt. %, of branched alkanes. In some aspects, the linear alkane product can contain greater than 0 wt. %, at least 0.1 wt. %, at least 0.25 wt. %, or at least 0.4 wt. %, of branched alkanes, and therefore, the linear alkane product can contain an amount of branched alkanes in a range from any minimum amount disclosed herein to any maximum amount disclosed herein.

Referring now to FIG. 1, this schematic flow diagram illustrates a process 100 for producing linear internal olefins and linear alkanes consistent with aspects of this invention. The olefin feed 110, which contains vinylidenes, a normal alpha olefin and/or linear internal olefins, is contacted 115 with a first acid catalyst (e.g., a solid acid catalyst) and a carboxylic acid, and a first reaction product 120 is formed. The first reaction product 120 contains linear internal olefins, trisubstituted olefins, and secondary esters. The secondary esters 130 are removed 125 from the first reaction product 120, and the secondary esters 130 are contacted 135 with a second acid catalyst (e.g., a solid acid catalyst), thereby forming a second reaction product 140. The second reaction product 140 contains linear internal olefins. A linear internal olefin product 150 is formed by removing 145 linear internal olefins from the second reaction product 140. In FIG. 1, the linear internal olefin product 150 is hydrogenated 155 to form a linear alkane product 160.

Acid Catalysts and Solid Acid Catalysts

In step (a) of the processes disclosed herein, the olefin feed comprising $C_{10}$ to $C_{20}$ vinylidenes and a $C_{10}$ to $C_{20}$ normal alpha olefin and/or $C_{10}$ to $C_{20}$ linear internal olefins, a first acid catalyst, and a $C_1$ to $C_{18}$ carboxylic acid are contacted to form a first reaction product comprising linear internal olefins, trisubstituted olefins, and secondary esters. In step (c), the secondary esters are contacted with a second acid catalyst to form a second reaction product comprising linear internal olefins.

Any suitable acid catalyst can be used as the first acid catalyst and the second acid catalyst, and the first acid catalyst and the second acid catalyst can be the same or different. In one aspect, one or both of the first acid catalyst and the second acid catalyst can be any suitable anhydrous acid or mineral acid, non-limiting examples of which include sulfuric acid, p-toluene sulfonic acid, methane sulfonic acid, and other sulfonic acids. In another aspect, one or both of the first acid catalyst and the second acid catalyst can be a solid acid catalyst. Any suitable solid acid catalyst can be used as the first acid catalyst and the second acid catalyst, and the first (solid) acid catalyst and the second (solid) acid catalyst can be the same or different. A particular benefit of using a solid acid catalyst is the ease of separating the respective solid catalyst from the first reaction product and the second reaction product. For instance, filtration can be used to separate the solid catalyst from the first reaction product and the second reaction product.

Illustrative and representative examples of suitable solid acid catalysts can include solid acid catalyst resins, such as acidic ion exchange resins. Solid acid catalyst resins can include a styrene-divinylbenzene resin, a functionalized styrene-divinylbenzene resin, a 4-vinylpyridine divinylbenzene resin, a functionalized 4-vinylpyridine divinylbenzene resin, an ionomer resin, a tetrafluoroethylene polymer resin modified with perfluorovinyl ether groups terminated with sulfonate groups, or any combination thereof; alternatively, a styrene-divinylbenzene resin, a 4-vinylpyridine divinylbenzene resin, an ionomer resin, a tetrafluoroethylene resin modified with perfluorovinyl ether groups terminated with sulfonate groups, and the like, as well as combinations thereof; or alternatively, a sulfonated copolymer of styrene-divinylbenzene. Some of these solid acid catalyst types are available under the Amberlyst® resin and Nafion® resin tradenames.

It can be beneficial for the (first or second) solid acid catalyst used in the disclosed processes to be dry and substantially free of water/moisture. The solid acid catalyst often contains less than or equal to 1 wt. % water/moisture, and in some aspects, the water/moisture content of the solid acid catalyst can be less than or equal to 0.5 wt. %, less than or equal to 1000 ppm (by weight), less than or equal to 500 ppm, or less than or equal to 200 ppm water/moisture, but often greater than 0 ppm, at least 1 ppm, at least 10 ppm, at least 25 ppm, or at least 50 ppm water/moisture.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Gas Chromatograph (GC) analyses were conducted on an Agilent 7890 GC System, using a HP-Innowax column (polyethyleneglycol, capillary 30 m×0.25 mm×25 μm nominal), with 40° C. temperature hold for 2 minutes followed by ramping at a rate of 8° C./min from 40° C. to 220° C., then 15° C./min to 270° C., which is held for 15 minutes. GC analysis column eluents were determined using a flame ionization detector. Standards were used to identify the reactants and products, and to monitor the course of the reactions.

Example 1

1-tetradecene and propionic acid

An equimolar mixture of commercially available 1-tetradecene (containing approximately 5 wt. % vinylidenes and 95 wt. % linear alpha olefin) and propionic acid was passed over a fixed bed containing 200 g of dry Amberlyst® 15 solid acid catalyst at 90° C., atmospheric pressure, and 1.0 WHSV, resulting in a first reaction product containing approximately 30 wt. % tetradecyl propionates. The initial 1-tetradecene underwent concurrent double bond isomerization to give 2, 3, 4, 5, 6, and 7-tetradecenes, which is shown in the top gas chromatogram plot of FIG. 2 (tetradecyl propionates and propionic acid are not shown). The first reaction product contained approximately 3.6 wt. % $C_{14}$ trisubstituted olefins, 2.4 wt. % $C_{14}$ linear alpha olefin, 44.8 wt. % $C_{14}$ linear internal olefins, 19.2 wt. % propionic acid, and 30 wt. % tetradecyl propionates.

Figure 2:
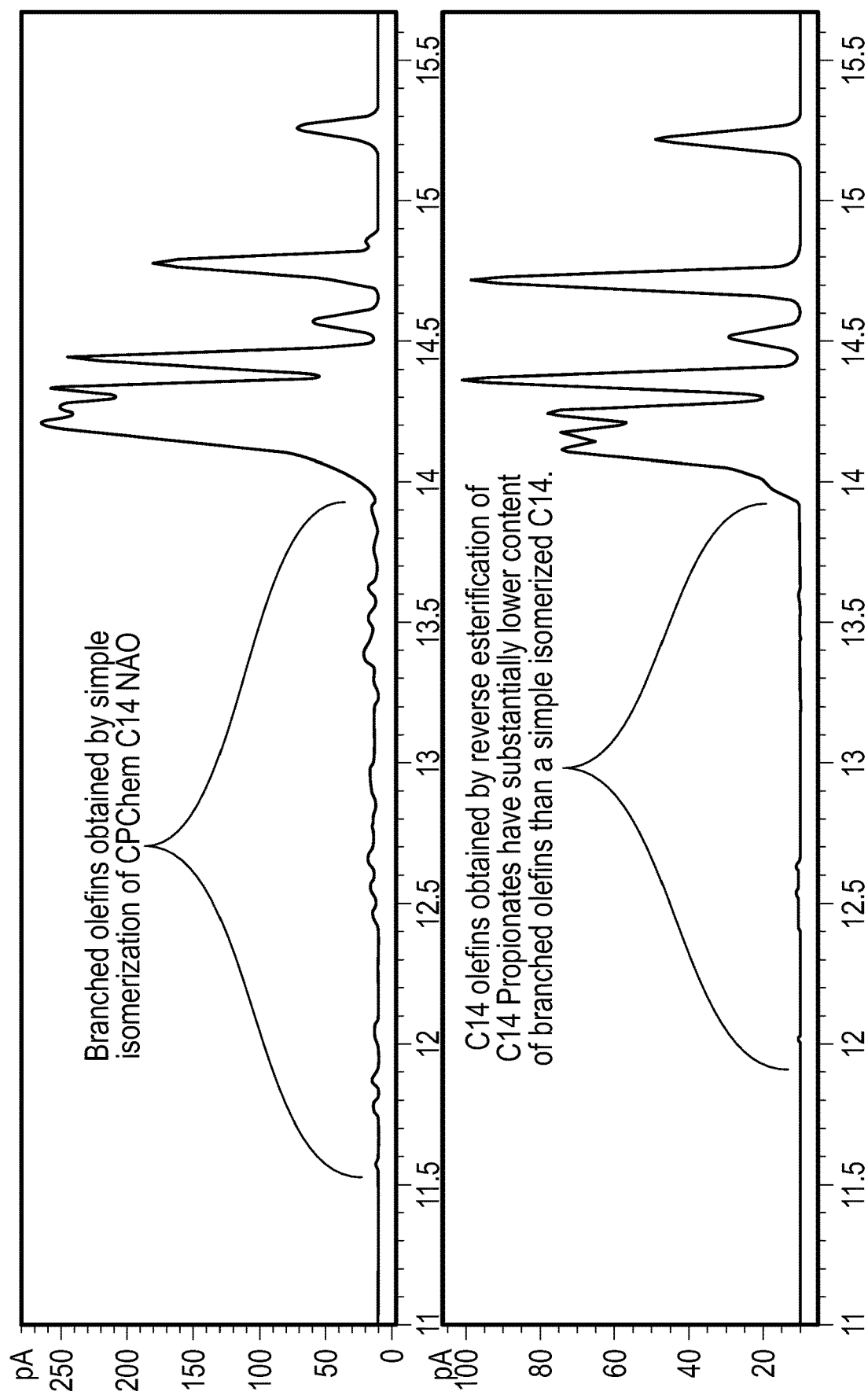
FIG. 2 presents gas chromatogram plots relating to the process described in Example 1.

The tetradecyl propionates were separated from the residual propionic acid and the tetradecenes by distillation. The mixture of tetradecyl propionates, which contained about 1 wt. % residual tetradecenes, was then stirred with 10 wt. % dry Amberlyst® 15 at 90° C. for 2 hr at atmospheric pressure. The tetradecyl propionates underwent reverse esterification, resulting in a second reaction product containing propionic acid and linear tetradecenes (less than 1 wt. % branched olefins and greater than 99 wt. % linear olefins). The bottom plot of FIG. 2 is a gas chromatogram of the tetradecenes formed in this reverse esterification. The tetradecenes from the reverse reaction of tetradecyl propionates had a substantially lower content of branched olefins than did the original 1-tetradecene sample. The branched tetradecenes did not react readily with propionic acid to form esters, while the linear tetradecenes reacted with propionic acid to form esters.

Constructive Example 2

Octadecenes and Heptanoic Acid

A mixture of 100 g of octadecenes (30 wt. % vinylidenes/trisubstituted olefins, 69 wt. % linear internal octadecenes, 1 wt. % 1-octadecene) and 51.5 g of heptanoic acid is stirred at 100° C. and atmospheric pressure with 20 g of dry Amberlyst® 15 solid acid catalyst until the first reaction product contains ~24 wt. % octadecyl heptanoates by GC-FID analysis. At this time, the first reaction product also can contain 26 wt. % heptanoic acid and 50 wt. % octadecenes. The liquid component is separated from the solid catalyst, and then the heptanoic acid and octadecenes are distilled overhead to yield approximately 37 g of a mixture of octadecyl heptanoates as the bottoms product. This mixture contains less than 0.5 wt. % octadecenes.

Next, the 37 g mixture of octadecyl heptanoates is stirred with 5 g of dry Amberlyst® 15 at 100° C. and atmospheric pressure until the second reaction product contains 40 wt. % octadecenes. The liquid component is then separated from the solid catalyst, and the octadecenes are isolated from the rest of the second reaction product by distillation. The linear octadecenes are hydrogenated with a suitable hydrogenation catalyst (e.g., a supported Nickel catalyst) to convert them to linear octadecanes. The octadecane product is approximately 99 wt. % linear octadecane and less than 1 wt. % branched octadecanes. The linearity of the $C_{18}$ hydrocarbon is increased from 70 wt. % in the starting octadecene feed stream to over 99 wt. %.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process comprising (a) contacting an olefin feed comprising $C_{10}$ to $C_{20}$ vinylidenes and a $C_{10}$ to $C_{20}$ normal alpha olefin and/or $C_{10}$ to $C_{20}$ linear internal olefins, a first acid catalyst, and a $C_1$ to $C_{18}$ carboxylic acid to form a first reaction product comprising linear internal olefins, trisubstituted olefins, and secondary esters, (b) removing all or a portion of the secondary esters from the first reaction product, (c) contacting the secondary esters and a second acid catalyst to form a second reaction product comprising linear internal olefins, and (d) removing all or a portion of the linear internal olefins from the second reaction product to form a linear internal olefin product.

Aspect 2. The process defined in aspect 1, further comprising (e) hydrogenating the linear internal olefin product to form a linear alkane product.

Aspect 3. The process defined in aspect 1 or 2, wherein the olefin feed comprises any $C_{10}$ to $C_{20}$ vinylidenes (and $C_{10}$ to $C_{20}$ normal alpha olefin and/or $C_{10}$ to $C_{20}$ linear internal olefins) disclosed herein, e.g., $C_{12}$ to $C_{20}$ vinylidenes (and a $C_{12}$ to $C_{20}$ normal alpha olefin and/or $C_{12}$ to $C_{20}$ linear internal olefins), $C_{14}$ to $C_{18}$ vinylidenes (and a $C_{14}$ to $C_{18}$ normal alpha olefin and/or $C_{14}$ to $C_{18}$ linear internal olefins), $C_{16}$ to $C_{18}$ vinylidenes (and a $C_{16}$ to $C_{18}$ normal alpha olefin and/or $C_{16}$ to $C_{18}$ linear internal olefins), Aspect 4. The process defined in any one of aspects 1-3, wherein the olefin feed comprises any $C_{10}$ to $C_{20}$ normal alpha olefin disclosed herein, e.g., 1-decene, 1-dodecene, 1-tetradecene, 1-hexadecene, 1-octadecene, or any combination thereof.

Aspect 5. The process defined in any one of aspects 1-4, wherein the olefin feed comprises any amount of the $C_{10}$ to $C_{20}$ normal alpha olefin and/or $C_{10}$ to $C_{20}$ linear internal olefins disclosed herein, e.g., at least 50 wt. %, at least 70 wt. %, at least 90 wt. %, at least 92 wt. %, or at least 95 wt. %, and less than or equal to 99 wt. %, less than or equal to 98 wt. %, or less than or equal to 97 wt. %, and/or the olefin feed comprises any weight ratio of $C_{10}$ to $C_{20}$ normal alpha olefin to $C_{10}$ to $C_{20}$ linear internal olefins disclosed herein, e.g., from 100:1 to 1:100, from 50:1 to 1:50, from 10:1 to 1:10, from 5:1 to 1:5, or from 2:1 to 1:2.

Aspect 6. The process defined in any one of aspects 1-5, wherein the olefin feed comprises any amount of $C_{10}$ to $C_{20}$ vinylidenes disclosed herein, e.g., less than or equal to 50 wt. %, less than or equal to 35 wt. %, less than or equal to 20 wt. %, or less than or equal to 10 wt. %, and at least 1 wt. %, at least 1.5 wt. %, at least 2 wt. %, at least 4 wt. %, or at least 5 wt. %.

Aspect 7. The process defined in any one of aspects 1-6, wherein the first acid catalyst (or the second acid catalyst) comprises any suitable acid catalyst herein (e.g., sulfuric acid, a sulfonic acid) or any suitable solid acid catalyst disclosed herein (e.g., an acidic ion exchange resin).

Aspect 8. The process defined in any one of aspects 1-6, wherein the first acid catalyst (or the second acid catalyst) is a solid acid catalyst comprising any functionalized styrene-divinylbenzene polymer, any 4-vinylpyridine divinylbenzene polymer, or any tetrafluoroethylene polymer modified with perfluorovinyl ether groups terminated with sulfonate groups disclosed herein, as well as combinations thereof.

Aspect 9. The process defined in any one of aspects 1-6, wherein the first acid catalyst (or the second acid catalyst) is a solid acid catalyst comprising a sulfonated copolymer of styrene-divinylbenzene.

Aspect 10. The process defined in any one of aspects 1-9, wherein the first acid catalyst (or the second acid catalyst) is a solid acid catalyst comprising any suitable amount of water/moisture, e.g., less than or equal to 1 wt. %, less than or equal to 0.5 wt. %, less than or equal to 1000 ppm, less than or equal to 500 ppm, or less than or equal to 200 ppm, and greater than 0 ppm, at least 1 ppm, at least 10 ppm, at least 25 ppm, or at least 50 ppm.

Aspect 11. The process defined in any one of aspects 1-10, wherein the carboxylic acid comprises any $C_1$ to $C_{18}$ carboxylic acid disclosed herein, e.g., a $C_1$ to $C_{12}$ carboxylic acid, a $C_1$ to $C_8$ carboxylic acid, a $C_2$ to $C_8$ carboxylic acid, or a $C_{12}$ to $C_{18}$ carboxylic acid.

Aspect 12. The process defined in any one of aspects 1-10, wherein the carboxylic acid comprises formic acid, acetic acid, propionic acid, butyric acid, pentanoic acid, hexanoic acid, heptanoic acid, octanoic acid, nonanoic acid, decanoic acid, or any combination thereof.

Aspect 13. The process defined in any one of aspects 1-12, wherein an amount of the carboxylic acid, based on the olefin feed, is in any range disclosed herein, e.g., less than or equal to 75 wt. %, less than or equal to 60 wt. %, or less than or equal to 50 wt. %, and at least 1 wt. %, at least 5 wt. %, at least 10 wt. %, at least 20 wt. %, or at least 25 wt. %, and/or a molar ratio of moles of the carboxylic acid to moles of olefin in the olefin feed in step (a) is in any range disclosed herein, e.g., from 10:1 to 1:10, from 5:1 to 1:5, from 4:1 to 1:4, from 3:1 to 1:3, from 1.5:1 to 1:1.5, or from 1.2:1 to 1:1.2 (carboxylic acid:olefin).

Aspect 14. The process defined in any one of aspects 1-13, wherein a mixture of the olefin feed and the carboxylic acid is contacted with the acid catalyst (or solid acid catalyst) in step (a).

Aspect 15. The process defined in any one of aspects 1-14, wherein step (a) (or step (c)) is conducted in the presence of any suitable amount of water/moisture, e.g., less than or equal to 1 wt. %, less than or equal to 0.5 wt. %, less than or equal to 1000 ppm, less than or equal to 500 ppm, or less than or equal to 200 ppm, and greater than 0 ppm, at least 1 ppm, at least 10 ppm, at least 25 ppm, or at least 50 ppm.

Aspect 16. The process defined in any one of aspects 1-15, wherein step (a) (or step (c)) is conducted at any temperature disclosed herein, e.g., from 10° C. to 120° C., from 20° C. to 110° C., from 20° C. to 100° C., from 50° C. to 110° C., from 70° C. to 110° C., or from 80° C. to 105° C.

Aspect 17. The process defined in any one of aspects 1-16, wherein step (a) (or step (c)) is conducted at any pressure disclosed herein, e.g., from 5 psig to 100 psig, at atmospheric pressure, or at a sub-atmospheric pressure.

Aspect 18. The process defined in any one of aspects 1-17, wherein step (a) (or step (c)) is conducted in the presence of a non-olefin solvent, and an amount of the non-olefin solvent, based on the olefin feed (or based on the secondary esters), is in any range disclosed herein, e.g., less than or equal to 25 wt. %, less than or equal to 10 wt. %, or less than or equal to 5 wt. %, and greater than 0 wt. %, at least 0.5 wt. %, at least 1 wt. %, or at least 2 wt. %.

Aspect 19. The process defined in any one of aspects 1-18, wherein a weight ratio of the olefin feed to the first acid catalyst (or a weight ratio of the secondary esters to the second acid catalyst) is in any range of weight ratios disclosed herein, e.g., from 1:1 to 100:1, from 1:1 to 10:1, from 1.5:1 to 40:1, or from 1.5:1 to 15:1.

Aspect 20. The process defined in any one of aspects 1-18, wherein step (a) (or step (c)) is conducted in a fixed bed reactor, and wherein the olefin feed and the first (solid) acid catalyst (or the secondary esters and the second (solid) acid catalyst) are contacted at a WHSV in any range of WHSVs disclosed herein, e.g., from 0.05 to 5, from 0.1 to 2, or from 0.2 to 1.

Aspect 21. The process defined in any one of aspects 1-20, wherein the first reaction product comprises any amount of $C_{10}$ to $C_{20}$ normal alpha olefin disclosed herein, e.g., less than or equal to 10 wt. %, less than or equal to 8 wt. %, less than or equal to 5 wt. %, less than or equal to 3 wt. %, or less than or equal to 1 wt. %, and greater than 0 wt. %, at least 0.1 wt. %, at least 0.5 wt. %, or at least 0.75 wt. %.

Aspect 22. The process defined in any one of aspects 1-21, wherein the first reaction product comprises any amount of dimer disclosed herein, e.g., less than or equal to 10 wt. %, less than or equal to 8 wt. %, less than or equal to 5 wt. %, less than or equal to 3 wt. %, or less than or equal to 1 wt. %, and greater than 0 wt. %, at least 0.1 wt. %, at least 0.5 wt. %, or at least 0.75 wt. %.

Aspect 23. The process defined in any one of aspects 1-22, wherein the first reaction product comprises, e.g., less than or equal to 5 wt. %, less than or equal to 4 wt. %, less than or equal to 2 wt. %, less than or equal to 1 wt. %, or less than or equal to 0.5 wt. %, more branched olefins than an amount of branched olefins in the olefin feed.

Aspect 24. The process defined in any one of aspects 1-23, wherein the first reaction product comprises a nearly equilibrium distribution of linear double bond isomers.

Aspect 25. The process defined in any one of aspects 1-24, wherein the first reaction product comprises any amount of trisubstituted olefins disclosed herein, e.g., e.g., less than or equal to 15 wt. %, less than or equal to 12 wt. %, less than or equal to 10 wt. %, or less than or equal to 8 wt. %, and at least 1 wt. %, at least 1.5 wt. %, at least 2 wt. %, at least 4 wt. %, or at least 5 wt. %.

Aspect 26. The process defined in any one of aspects 1-25, wherein the first reaction product comprises any amount of secondary esters disclosed herein, e.g., from 10 to 50 mol %, from 20 to 50 mol %, from 25 to 50 mol %, or from 30 to 50 mol %, based on the moles of the $C_{10}$ to $C_{20}$ normal alpha olefin and/or $C_{10}$ to $C_{20}$ linear internal olefins in the olefin feed.

Aspect 27. The process defined in any one of aspects 1-26, wherein step (b) is performed using any technique disclosed herein, e.g., flashing, wiped film evaporation, distillation, short path distillation, or any combination thereof.

Aspect 28. The process defined in any one of aspects 1-27, wherein the linear internal olefins, the trisubstituted olefins, and/or residual carboxylic acid is/are recovered from the first reaction product (and optionally recycled).

Aspect 29. The process defined in any one of aspects 1-28, wherein the second reaction product comprises any amount of linear internal olefin disclosed herein, e.g., at least 90 wt. %, at least 95 wt. %, at least 97 wt. %, at least 98 wt. %, or at least 99 wt. %, and less than 100 wt. %, less than or equal to 99.99 wt. %, less than or equal to 99.9 wt. %, or less than or equal to 99.5 wt. % (based on hydrocarbons).

Aspect 30. The process defined in any one of aspects 1-29, wherein the second reaction product comprises any amount of branched olefins disclosed herein, e.g., less than or equal to 4 wt. %, less than or equal to 3 wt. %, less than or equal to 2 wt. %, less than or equal to 1 wt. %, or less than or equal to 0.5 wt. %, and greater than 0 wt. %, at least 0.1 wt. %, at least 0.25 wt. %, or at least 0.4 wt. % (based on hydrocarbons).

Aspect 31. The process defined in any one of aspects 1-30, wherein the second reaction product further comprises the $C_1$ to $C_{18}$ carboxylic acid.

Aspect 32. The process defined in any one of aspects 1-31, wherein step (d) is performed using any technique disclosed herein, e.g., flashing, wiped film evaporation, distillation, short path distillation, or any combination thereof.

Aspect 33. The process defined in any one of aspects 1-32, wherein residual ester and/or carboxylic acid is/are recovered from the second reaction product (and optionally recycled).

Aspect 34. The process defined in any one of aspects 1-33, wherein the linear internal olefin product comprises any amount of linear internal olefin disclosed herein, e.g., at least 90 wt. %, at least 95 wt. %, at least 97 wt. %, at least 98 wt. %, or at least 99 wt. %, and less than 100 wt. %, less than or equal to 99.99 wt. %, less than or equal to 99.9 wt. %, or less than or equal to 99.5 wt. %.

Aspect 35. The process defined in any one of aspects 1-34, wherein the linear internal olefin product comprises any amount of branched olefins disclosed herein, e.g., less than or equal to 4 wt. %, less than or equal to 3 wt. %, less than or equal to 2 wt. %, less than or equal to 1 wt. %, or less than or equal to 0.5 wt. %, and greater than 0 wt. %, at least 0.1 wt. %, at least 0.25 wt. 15%, or at least 0.4 wt. %.

Aspect 36. The process defined in any one of aspects 2-35, wherein the linear alkane product comprises any amount of linear alkane disclosed herein, e.g., at least 90 wt. %, at least 95 wt. %, at least 97 wt. %, at least 98 wt. %, or at least 99 wt. %, and less than 100 wt. %, less than or equal to 99.99 wt. %, less than or equal to 99.9 wt. %, or less than or equal to 99.5 wt. %. Aspect 37. The process defined in any one of aspects 2-36, wherein the linear alkane product comprises any amount of branched alkanes disclosed herein, e.g., less than or equal to 4 wt. %, less than or equal to 3 wt. %, less than or equal to 2 wt. %, less than or equal to 1 wt. %, or less than or equal to 0.5 wt. %, and greater than 0 wt. %, at least 0.1 wt. %, at least 0.25 wt. %, or at least 0.4 wt. %.

I claim:
1. A process comprising:
   (a) contacting an olefin feed comprising $C_{10}$ to $C_{20}$ vinylidenes and a $C_{10}$ to $C_{20}$ normal alpha olefin and/or $C_{10}$ to $C_{20}$ linear internal olefins, a first acid catalyst, and a $C_1$ to $C_{18}$ carboxylic acid to form a first reaction product comprising linear internal olefins, trisubstituted olefins, and secondary esters;
   (b) removing all or a portion of the secondary esters from the first reaction product to form a secondary ester product;
   (c) contacting the secondary ester product and a second acid catalyst at a temperature from 50° C. to 120° C. to form a second reaction product comprising linear internal olefins, wherein the second acid catalyst comprises a solid acid catalyst resin; and

(d) removing all or a portion of the linear internal olefins from the second reaction product to form a linear internal olefin product.

2. The process of claim 1, wherein the first acid catalyst and the second acid catalyst independently comprise a sulfonated copolymer of styrene-divinylbenzene.

3. The process of claim 1, wherein the olefin feed comprises:
from 50 wt. % to 99 wt. % of the $C_{10}$ to $C_{20}$ normal alpha olefin and/or $C_{10}$ to $C_{20}$ linear internal olefins; and
from 1 wt. % to 50 wt. % of Cm to $C_{20}$ vinylidenes.

4. The process of claim 3, wherein the $C_{10}$ to $C_{20}$ normal alpha olefin comprises 1-decene, 1-dodecene, 1-tetradecene, 1-hexadecene, 1-octadecene, or any combination thereof.

5. The process of claim 1, wherein:
a molar ratio of moles of the carboxylic acid to moles of olefin in the olefin feed in step (a) is from 1:4 to 4:1; and
the carboxylic acid comprises formic acid, acetic acid, propionic acid, butyric acid, pentanoic acid, hexanoic acid, heptanoic acid, octanoic acid, nonanoic acid, decanoic acid, or any combination thereof.

6. The process of claim 1, wherein a weight ratio of the olefin feed to the acid catalyst in step (a) is from 1:1 to 100:1.

7. The process of claim 1, wherein the first reaction product comprises:
less than or equal to 10 wt. % of $C_{10}$ to $C_{20}$ normal alpha olefin;
less than or equal to 10 wt. % of dimer; and
less than or equal to 2 wt. % more branched olefins than an amount of branched olefins in the olefin feed.

8. The process of claim 1, wherein the first reaction product comprises:
from 1 wt. % to 15 wt. % of the trisubstituted olefins; and
from 10 to 50 mol % of the secondary esters, based on moles of the $C_{10}$ to $C_{20}$ normal alpha olefin and/or $C_{10}$ to $C_{20}$ linear internal olefins in the olefin feed.

9. The process of claim 1, wherein the removing in step (b) comprises flashing, wiped film evaporation, distillation, short path distillation, or any combination thereof.

10. The process of claim 1, wherein a weight ratio of the secondary esters to the second acid catalyst in step (c) is from 1:1 to 100:1.

11. The process of claim 1, wherein the second reaction product comprises, based on hydrocarbons:
at least 95 wt. % linear internal olefins; and
less than or equal to 4 wt. % branched olefins.

12. The process of claim 1, wherein removing in step (d) comprises flashing, wiped film evaporation, distillation, short path distillation, or any combination thereof.

13. The process of claim 1, wherein the linear internal olefin product comprises:
at least 95 wt. % linear internal olefins; and
less than or equal to 4 wt. % branched olefins.

14. The process of claim 1, wherein the linear internal olefin product comprises:
at least 99 wt. % linear internal olefins; and
less than or equal to 1 wt. % branched olefins.

15. The process of claim 1, further comprising a step of (e) hydrogenating the linear internal olefin product to form a linear alkane product.

16. The process of claim 15, wherein the linear alkane product comprises:
at least 95 wt. % linear alkane; and
less than or equal to 4 wt. % branched alkanes.

17. The process of claim 15, wherein the linear alkane product comprises:
at least 99 wt. % linear alkane; and
less than or equal to 1 wt. % branched alkanes.

18. The process of claim 17, wherein the first acid catalyst and the second acid catalyst independently comprise a sulfonated copolymer of styrene-divinylbenzene.

19. The process of claim 17, wherein:
the $C_{10}$ to $C_{20}$ normal alpha olefin comprises 1-decene, 1-dodecene, 1-tetradecene, 1-hexadecene, 1-octadecene, or any combination thereof; and
the linear alkane comprises decane, dodecane, tetradecane, hexadecane, octadecane, or any combination thereof.

20. The process of claim 17, wherein:
the removing in step (b) comprises flashing, wiped film evaporation, distillation, short path distillation, or any combination thereof; and
the removing in step (d) comprises flashing, wiped film evaporation, distillation, short path distillation, or any combination thereof.

21. A process comprising:
(a) contacting an olefin feed comprising $C_{10}$ to $C_{20}$ vinylidenes and a $C_{10}$ to $C_{20}$ normal alpha olefin and/or $C_{10}$ to $C_{20}$ linear internal olefins, a first acid catalyst, and a Ci to Cis carboxylic acid to form a first reaction product comprising linear internal olefins, trisubstituted olefins, and secondary esters;
(b) removing all or a portion of the secondary esters from the first reaction product to form a secondary ester product;
(c) contacting the secondary ester product and a second acid catalyst comprising a solid acid catalyst resin at a temperature from 80° C. to 150° C. to form a second reaction product comprising, based on hydrocarbons:
at least 95 wt. % linear internal olefins; and
less than or equal to 4 wt. % branched olefins; and
(d) removing all or a portion of the linear internal olefins from the second reaction product to form a linear internal olefin product.

22. The process of claim 21, wherein the linear internal olefin product comprises at least 99 wt. % linear internal olefins.

23. The process of claim 22, further comprising a step of (e) hydrogenating the linear internal olefin product to form a linear alkane product.

24. The process of claim 23, wherein the linear alkane product comprises decane, dodecane, tetradecane, hexadecane, octadecane, or any combination thereof.

25. The process of claim 21, wherein the olefin feed comprises:
from 50 wt. % to 99 wt. % of the $C_{10}$ to $C_{20}$ normal alpha olefin and/or $C_{10}$ to $C_{20}$ linear internal olefins; and
from 1 wt. % to 50 wt. % of he $C_{10}$ to $C_{20}$ vinylidenes.

26. The process of claim 25, wherein:
the $C_{10}$ to $C_{20}$ normal alpha olefin comprises 1-decene, 1-dodecene, 1-tetradecene, 1-hexadecene, 1-octadecene, or any combination thereof;
the first acid catalyst and the second acid catalyst independently comprise a sulfonated copolymer of styrene-divinylbenzene; and
the carboxylic acid comprises formic acid, acetic acid, propionic acid, butyric acid, pentanoic acid, hexanoic acid, heptanoic acid, octanoic acid, nonanoic acid, decanoic acid, or any combination thereof.

27. The process of claim 26, wherein:
the removing in step (b) comprises flashing, wiped film evaporation, distillation, short path distillation, or any combination thereof; and
the removing in step (d) comprises flashing, wiped film evaporation, distillation, short path distillation, or any combination thereof.

\* \* \* \* \*